US012680094B2

(12) United States Patent (10) Patent No.: US 12,680,094 B2
Yamaguchi et al. (45) Date of Patent: Jul. 14, 2026

(54) NUCLEIC ACID PURIFICATION METHOD, NUCLEIC ACID EXTRACTION LIQUID, AND NUCLEIC ACID PURIFICATION KIT

(71) Applicants: SEKISUI MEDICAL CO., LTD., Tokyo (JP); SEKISUI CHEMICAL CO., LTD., Osaka (JP)

(72) Inventors: Sou Yamaguchi, Tokyo (JP); Katsura Uchida, Tokyo (JP); Tatsunori Takamatsu, Tokyo (JP); Takamasa Kouno, Osaka (JP); Takuya Kinoshita, Osaka (JP)

(73) Assignees: SEKISUI MEDICAL CO., LTD., Tokyo (JP); SEKISUI CHEMICAL CO., LTD., Osaka (JP)

( * ) Notice: Subject to any disclaimer, the term of this patent is extended or adjusted under 35 U.S.C. 154(b) by 602 days.

(21) Appl. No.: 18/024,322

(22) PCT Filed: Sep. 3, 2021

(86) PCT No.: PCT/JP2021/032411
§ 371 (c)(1),
(2) Date: Mar. 2, 2023

(87) PCT Pub. No.: WO2022/059516
PCT Pub. Date: Mar. 24, 2022

(65) Prior Publication Data
US 2024/0011013 A1 Jan. 11, 2024

(30) Foreign Application Priority Data
Sep. 15, 2020 (JP) ................................. 2020-154343

(51) Int. Cl.
*C12N 15/10* (2006.01)

(52) U.S. Cl.
CPC ................................. *C12N 15/1006* (2013.01)

(58) Field of Classification Search
CPC .................................................... C12N 15/1006
See application file for complete search history.

(56) References Cited

U.S. PATENT DOCUMENTS

| | | |
|---|---|---|
| 2006/0068491 A1 | 3/2006 | Makino et al. |
| 2014/0087366 A1* | 3/2014 | Srinivasan ............... C12Q 1/68 |
| 2022/0090048 A1* | 3/2022 | Kouno ................... C12N 15/10 |

FOREIGN PATENT DOCUMENTS

| | | |
|---|---|---|
| EP | 1 630 228 | 3/2006 |
| JP | 2005-17013 | 1/2005 |

(Continued)

OTHER PUBLICATIONS

Product sheet for Tween 20 (Item P1379) by Millipore Sigma (2025) Retrieved from the internet <www.sigmaaldrich.com> Retrieved on Jul. 20, 2025.*

(Continued)

*Primary Examiner* — Scarlett Y Goon
(74) *Attorney, Agent, or Firm* — Wenderoth, Lind & Ponack, L.L.P.

(57) ABSTRACT

Provided is a nucleic acid purification method capable of efficiently purifying a nucleic acid. The nucleic acid purification method including the steps of: mixing a nucleic acid with an antifoaming agent and a coprecipitation agent; and purifying the nucleic acid, in which the antifoaming agent is at least one of a nonionic surfactant and a silicone antifoaming agent.

9 Claims, 5 Drawing Sheets

(56)        References Cited

FOREIGN PATENT DOCUMENTS

| | | |
|----|----|----|
| JP | 2006-87372 | 4/2006 |
| JP | 2007-68452 | 3/2007 |
| JP | 2009-92592 | 4/2009 |
| JP | 2016-067291 | 5/2016 |
| WO | 2006/083017 | 8/2006 |
| WO | 2020/153248 | 7/2020 |
| WO | WO-2020257749 A1 * 12/2020 ............ C11D 11/02 |

OTHER PUBLICATIONS

English translation of International Preliminary Report on Patent-
ability and Written Opinion issued Mar. 21, 2023 in International
(PCT) Application No. PCT/JP2021/032411.
Extended European Search Report issued Sep. 18, 2024 in European
Patent Application No. 21869203.6.
International Search Report (ISR) issued Nov. 16, 2021 in Interna-
tional (PCT) Application No. PCT/JP2021/032411.

* cited by examiner

[FIG. 1.]
<u>1</u>
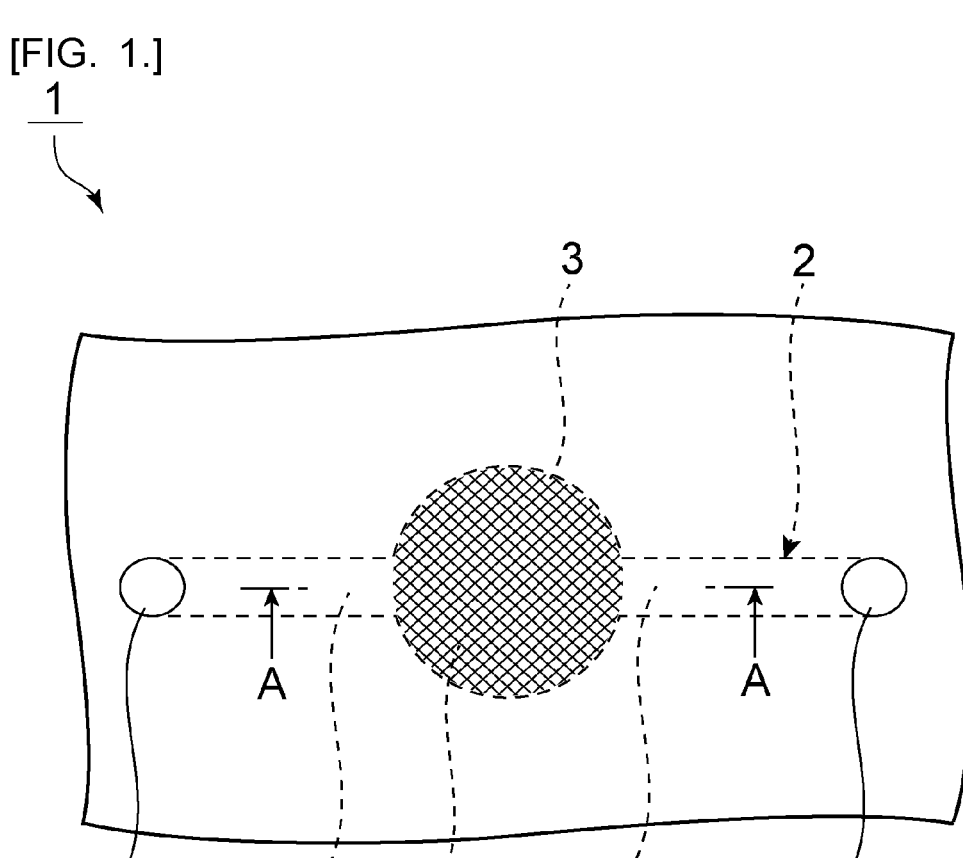
[FIG. 2.]
<u>1</u>
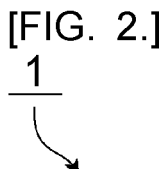
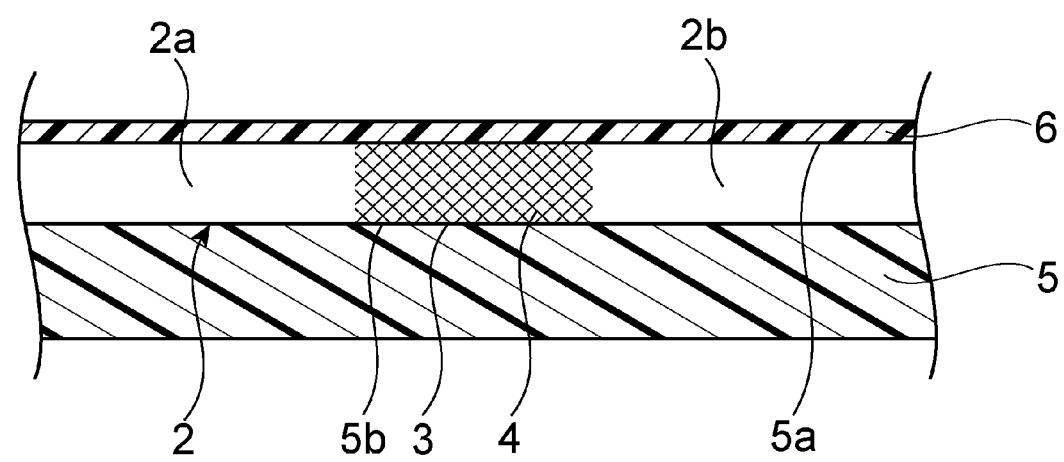

[FIG. 3.]
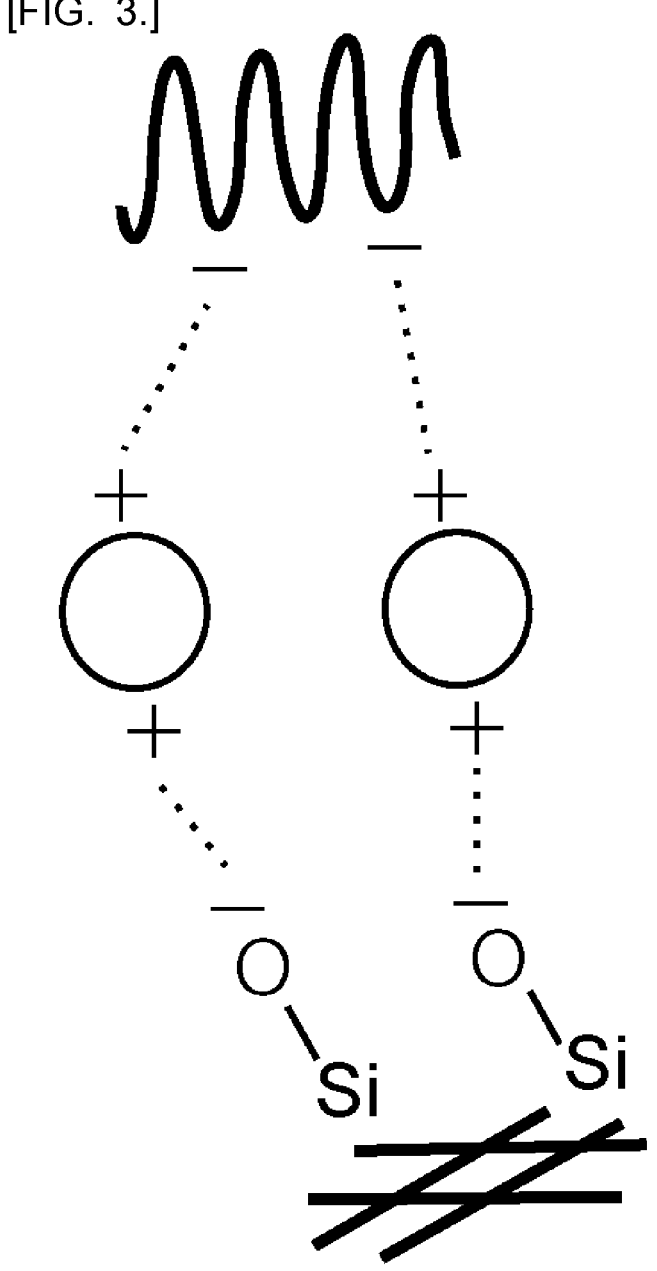

[FIG. 4.]
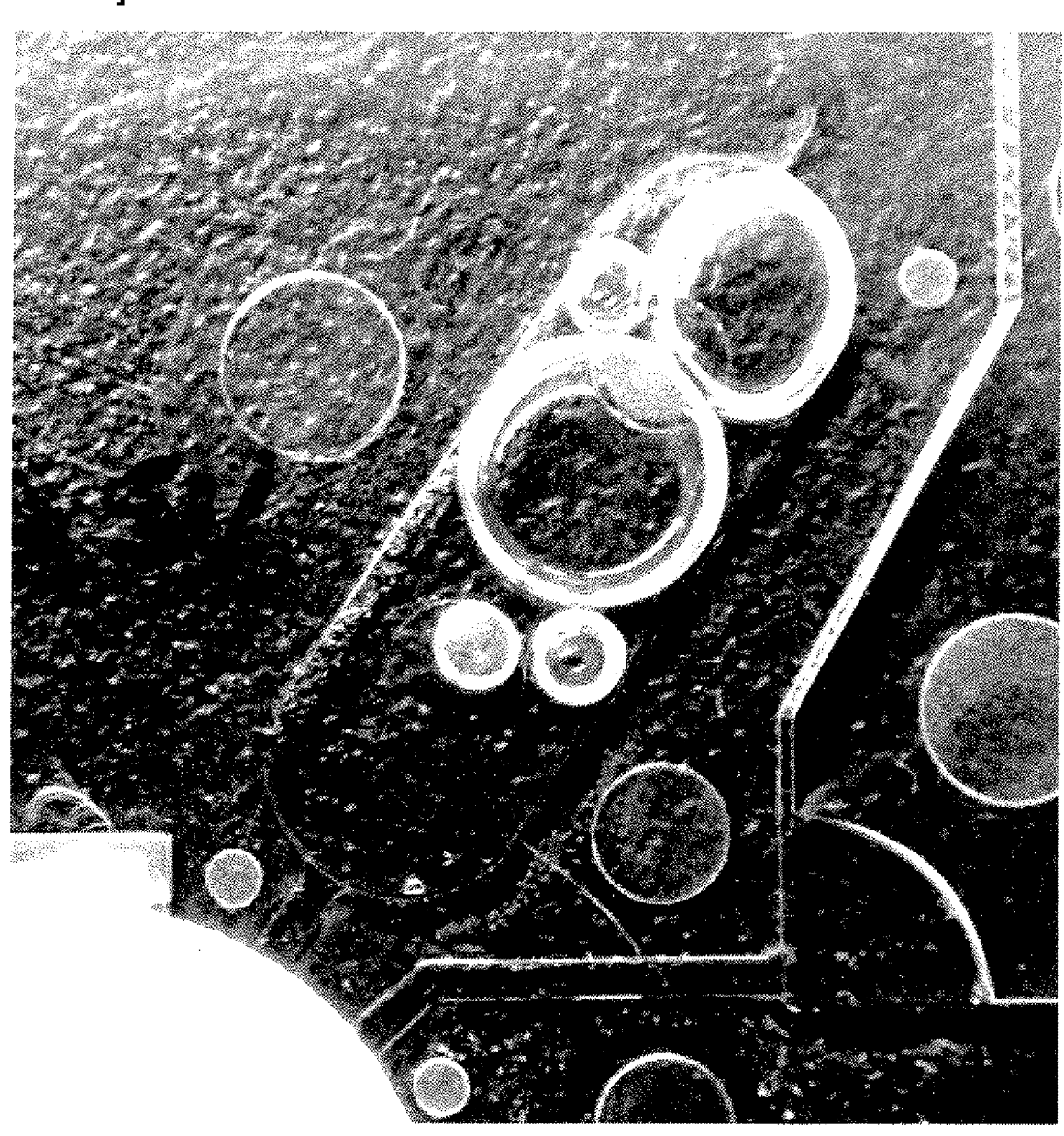

[FIG. 5.]
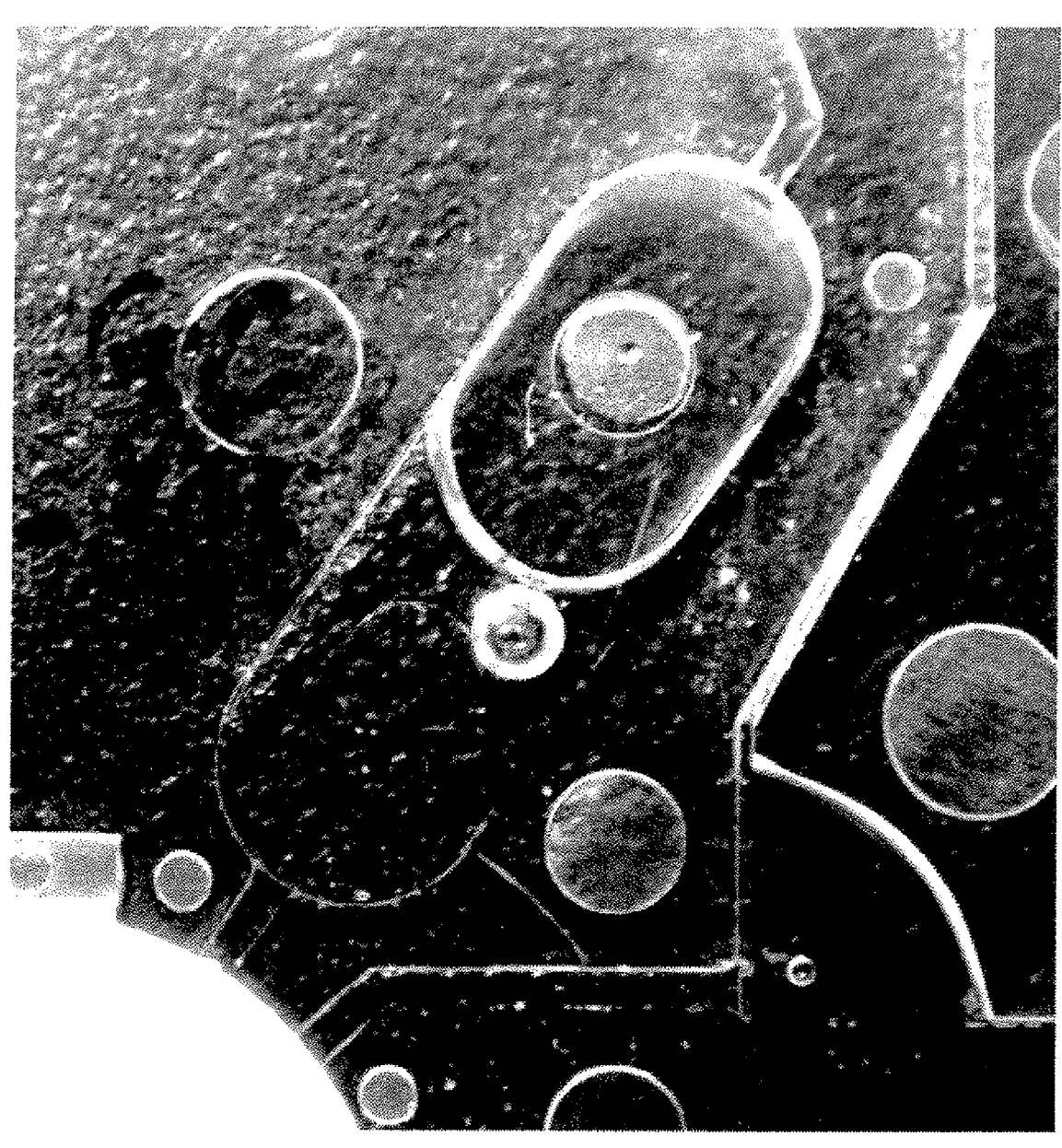

[FIG. 6.]
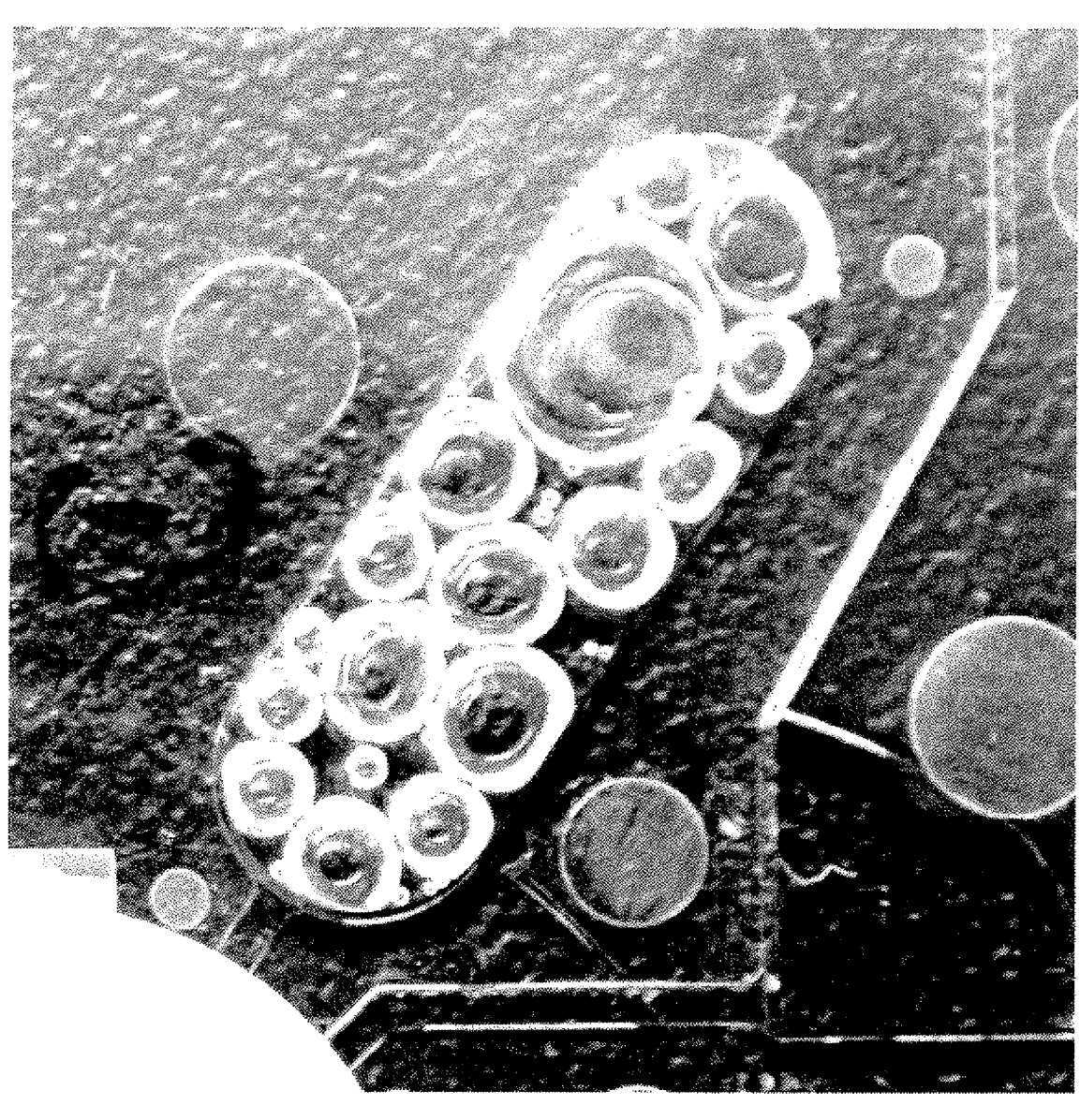

NUCLEIC ACID PURIFICATION METHOD, NUCLEIC ACID EXTRACTION LIQUID, AND NUCLEIC ACID PURIFICATION KIT

TECHNICAL FIELD

The present invention relates to a nucleic acid purification method, and a nucleic acid extraction liquid and a nucleic acid purification kit that are used in the nucleic acid purification method.

BACKGROUND ART

Conventionally, various methods for purifying nucleic acids such as RNA and DNA contained in samples such as viruses, bacteria, fungi, or cells have been studied. For example, a method is known in which a precipitation reagent such as alcohol is added to an extraction liquid containing a nucleic acid derived from a sample to precipitate the nucleic acid, the precipitated nucleic acid is adsorbed on a solid phase carrier, impurities such as proteins derived from the sample attached to the solid phase carrier together with the nucleic acid are washed, and then the nucleic acid is recovered by an eluate.

For example, Patent Document 1 below discloses a method for separating and purifying a nucleic acid using a microdevice. The method for separating and purifying a nucleic acid includes steps of: bringing a sample solution containing a nucleic acid into contact with a nucleic acid adsorptive carrier to adsorb the nucleic acid; washing the nucleic acid adsorptive carrier with a washing liquid in a state where the nucleic acid is adsorbed; and desorbing the nucleic acid from the nucleic acid adsorptive carrier with a recovery liquid to purify the nucleic acid.

Furthermore, Patent Document 1 describes that a pretreatment step of mixing and homogenizing a specimen and a nucleic acid solubilizing reagent to obtain the sample solution containing a nucleic acid may be included. It is described that the nucleic acid solubilizing reagent may be a solution containing at least one of a chaotropic salt, a surfactant, a proteolytic enzyme, an antifoaming agent, and a nucleic acid stabilizer.

PRIOR ART DOCUMENT

Patent Document

Patent Document 1: JP 2006-087372 A

SUMMARY OF THE INVENTION

Problem to be Solved by the Invention

Meanwhile, when a solution is delivered using a microchip, there is a problem that bubbles are generated and affect purification and detection of nucleic acid.

Even when the nucleic acid purification method of Patent Document 1 is used, generation of bubbles may not be sufficiently suppressed. In addition, even when the generation of bubbles can be suppressed, efficiency of nucleic acid recovery may not be sufficiently improved. Therefore, the nucleic acid purification method of Patent Document 1 has a problem that it is difficult to achieve both suppression of bubble generation and improvement of efficiency of nucleic acid recovery.

In addition, also in a nucleic acid purification method using a spin column or magnetic beads, there is a case where filter filtration of an extraction liquid is performed in order to remove impurities derived from a specimen, but there is a problem that handleability of the filter filtration is deteriorated due to an increase in filtration resistance due to viscosity derived from the specimen or foaming derived from the specimen.

Therefore, the conventional nucleic acid purification method has a problem that it is difficult to efficiently purify the nucleic acid.

An object of the present invention is to provide a nucleic acid purification method capable of efficiently purifying a nucleic acid, and a nucleic acid extraction liquid and a nucleic acid purification kit used in the nucleic acid purification method.

Means for Solving the Problem

A nucleic acid purification method according to the present invention includes the steps of: mixing a nucleic acid with an antifoaming agent and a coprecipitation agent; and purifying the nucleic acid, in which the antifoaming agent is at least one of a nonionic surfactant and a silicone antifoaming agent.

In a specific aspect of the nucleic acid purification method according to the present invention, the nucleic acid is mixed with the antifoaming agent and the coprecipitation agent, and then the nucleic acid is adsorbed on a solid phase carrier and purified.

Another specific aspect of the nucleic acid purification method according to the present invention further includes a step of preparing a nucleic acid extraction liquid containing the antifoaming agent and the coprecipitation agent in advance, in which a sample containing the nucleic acid is brought into contact with the nucleic acid extraction liquid to mix the nucleic acid with the antifoaming agent and the coprecipitation agent.

In still another specific aspect of the nucleic acid purification method according to the present invention, the antifoaming agent is a nonionic surfactant.

In still another specific aspect of the nucleic acid purification method according to the present invention, the nucleic acid purification method further includes a step of preparing a nucleic acid extraction liquid containing the antifoaming agent and the coprecipitation agent in advance, in which a content of the nonionic surfactant in the nucleic acid extraction liquid is 0.001 vol % or more and 1 vol % or less.

In still another specific aspect of the nucleic acid purification method according to the present invention, the nonionic surfactant is at least one selected from a group consisting of a polyoxyalkylene alkyl ether, a polyoxyethylene octylphenyl ether, a polyoxyethylene distyrenated phenyl ether, a polyoxyalkylene fatty acid ester, a polyoxyalkylene glyceryl ether, a sorbitan fatty acid ester, a lauryl-$\beta$-D-maltoside, a polyoxyethylene alkylamine, a palm kernel oil fatty acid diethanolamide, and a digitonin.

In still another specific aspect of the nucleic acid purification method according to the present invention, the nonionic surfactant is a mixture of a polyoxyalkylene alkyl ether and a polyoxyalkylene fatty acid ester.

In still another specific aspect of the nucleic acid purification method according to the present invention, the antifoaming agent is the silicone antifoaming agent.

In still another specific aspect of the nucleic acid purification method according to the present invention, the nucleic acid purification method further includes a step of preparing a nucleic acid extraction liquid containing the antifoaming agent and the coprecipitation agent in advance, in which a content of the silicone antifoaming agent in the nucleic acid extraction liquid is 0.001 vol % or more and 10 vol % or less.

In still another specific aspect of the nucleic acid purification method according to the present invention, the silicone antifoaming agent includes a silicone oil and an emulsifier.

In still another specific aspect of the nucleic acid purification method according to the present invention, the silicone antifoaming agent is obtained by emulsifying a silicone oil with a nonionic surfactant.

In still another specific aspect of the nucleic acid purification method according to the present invention, the coprecipitation agent is a polyadenine.

The nucleic acid extraction liquid according to the present invention is a nucleic acid extraction liquid used for nucleic acid purification, and contains an antifoaming agent and a coprecipitation agent, in which the antifoaming agent is at least one of a nonionic surfactant and a silicone antifoaming agent.

In a specific aspect of the nucleic acid extraction liquid according to the present invention, the antifoaming agent is the nonionic surfactant.

In another specific aspect of the nucleic acid extraction liquid according to the present invention, a content of the nonionic surfactant in the nucleic acid extraction liquid is 0.001 vol % or more and 1 vol % or less.

In still another specific aspect of the nucleic acid extraction liquid according to the present invention, the nonionic surfactant is at least one selected from a group consisting of a polyoxyalkylene alkyl ether, a polyoxyethylene branched alkyl ether, a polyoxyethylene octylphenyl ether, a polyoxyethylene distyrenated phenyl ether, a polyoxyethylene phytosteryl ether, a polyoxyalkylene fatty acid ester, a polyoxyalkylene glyceryl ether, a sorbitan fatty acid ester, a lauryl-β-D-maltoside, a polyoxyethylene alkylamine, a palm kernel oil fatty acid diethanolamide, and a digitonin.

In still another specific aspect of the nucleic acid extraction liquid according to the present invention, the nonionic surfactant is a mixture of a polyoxyalkylene alkyl ether and a polyoxyalkylene fatty acid ester.

In still another specific aspect of the nucleic acid extraction liquid according to the present invention, the antifoaming agent is the silicone antifoaming agent.

In still another specific aspect of the nucleic acid extraction liquid according to the present invention, a content of the silicone antifoaming agent in the nucleic acid extraction liquid is 0.001 vol % or more and 10 vol % or less.

In still another specific aspect of the nucleic acid extraction liquid according to the present invention, the silicone antifoaming agent includes a silicone oil and an emulsifier.

In still another specific aspect of the nucleic acid extraction liquid according to the present invention, the silicone antifoaming agent is obtained by emulsifying the silicone oil with the nonionic surfactant.

In still another specific aspect of the nucleic acid extraction liquid according to the present invention, the coprecipitation agent is a polyadenine.

The nucleic acid purification kit according to the present invention includes a nucleic acid extraction liquid configured according to the present invention.

Effect of the Invention

According to the present invention, it is possible to provide a nucleic acid purification method capable of efficiently purifying a nucleic acid, and a nucleic acid extraction liquid and a nucleic acid purification kit used in the nucleic acid purification method.

BRIEF DESCRIPTION OF THE DRAWINGS

FIG. 1 is a schematic plan view showing a microchip used in a nucleic acid purification method according to one embodiment of the present invention.

FIG. 2 is a schematic cross-sectional view of a portion taken along a line A-A in FIG. 1.

FIG. 3 is a schematic view for illustrating a state in which a nucleic acid is adsorbed on an anionic adsorbent in the nucleic acid purification method according to one embodiment of the present invention.

FIG. 4 is a photograph for confirming the number of bubbles generated during liquid delivery in Example 1.

FIG. 5 is a photograph for confirming the number of bubbles generated during the liquid delivery in Example 2.

FIG. 6 is a photograph for confirming the number of bubbles generated during the liquid delivery in Comparative Example 1.

MODE FOR CARRYING OUT THE INVENTION

The following will clarify the present invention by describing specific embodiments of the present invention with reference to the drawings.

[Nucleic Acid Purification Method and Nucleic Acid Extraction Liquid]

A nucleic acid purification method of the present invention includes a step of mixing a nucleic acid with an antifoaming agent and a coprecipitation agent, and a step of purifying the nucleic acid. In the present invention, the antifoaming agent is at least one of a nonionic surfactant and a silicone antifoaming agent.

The nucleic acid can be efficiently purified because the nucleic acid purification method of the present invention includes the step of mixing the nucleic acid with the antifoaming agent and the coprecipitation agent, and at least one of the nonionic surfactant and the silicone antifoaming agent is used as the antifoaming agent.

Conventionally, when a solution is delivered using a microchip, there has been a problem that bubbles are generated particularly when a highly viscous solution is delivered, and affect purification and detection of nucleic acid. When the nucleic acid concentration is low, there has been also a problem that nucleic acid purification efficiency particularly decreases. In addition, even when the generation of bubbles can be suppressed, there has been a problem that the efficiency of nucleic acid recovery cannot be sufficiently enhanced. Therefore, the conventional nucleic acid purification method has a problem that it is difficult to achieve both suppression of bubble generation and improvement of efficiency of nucleic acid recovery.

On the other hand, the present inventors have found that generation of bubbles can be suppressed by mixing a nucleic acid with the antifoaming agent that is at least one of the nonionic surfactant and the silicone antifoaming agent in a pre-step of purifying the nucleic acid. Furthermore, in this case, it has been found that the efficiency of nucleic acid recovery can be further enhanced by mixing the nucleic acid and the coprecipitation agent. In other words, the present inventors have found that, by mixing the nucleic acid with a specific antifoaming agent and the coprecipitation agent in the pre-step of purifying the nucleic acid, both suppression of bubble generation and improvement of efficiency of nucleic acid recovery can be achieved at a high level. Therefore, according to the nucleic acid purification method of the present invention, the nucleic acid can be efficiently purified. Accordingly, a sufficient amount of nucleic acid can be obtained by one purification treatment, so that sensitivity of analysis and examination in the subsequent steps can be enhanced.

(Nucleic Acid Extraction Liquid)

The nucleic acid extraction liquid of the present invention contains an antifoaming agent and a coprecipitation agent. The antifoaming agent is at least one of a nonionic surfactant and a silicone antifoaming agent.

The nonionic surfactant is not particularly limited, and examples thereof include a polyoxyalkylene alkyl ether, a polyoxyethylene branched alkyl ether, a polyoxyethylene octylphenyl ether, a polyoxyethylene distyrenated phenyl ether, a polyoxyethylene phytosteryl ether, a polyoxyalkylene fatty acid ester, a polyoxyalkylene glyceryl ether, a sorbitan fatty acid ester, a lauryl-β-D-maltoside, a polyoxyethylene alkylamine, a palm kernel oil fatty acid diethanolamide, a digitonin, a polyoxyethylene polyoxypropylene glycol, an alkyl polyglycoside, an alkyl alkanolamide, polyoxyethylene hydrogenated castor oil, a polyethylene glycol fatty acid ester, an alkyl glyceryl ether, a polyoxyethylene polyoxypropylene glycol, a polyoxyethylene alkyl ether, a polyoxyethylene sorbitol tetraoleate, a polyoxyethylene sorbitan fatty acid ester, a propylene glycol fatty acid ester, a glycerin fatty acid ester, and the like. Furthermore, examples of the polyoxyalkylene alkyl ether include a polyoxyethylene lauryl ether, a polyoxyethylene cetyl ether, a polyoxyethylene stearyl ether, and a polyoxyethylene oleyl ether. Moreover, examples of the polyoxyethylene branched alkyl ether include a polyoxyethylene isodecyl ether, a polyoxyethylene tridecyl ether, a polyoxyethylene octyldodecyl ether, and the like. These may be used singly or in combination of two or more kinds thereof.

The nonionic surfactant is preferably a mixture of a polyoxyalkylene alkyl ether and a polyoxyalkylene fatty acid ester. In this case, the generation of bubbles can be more reliably suppressed.

Furthermore, examples of the fatty acid constituting the fatty acid ester include a stearic acid, an oleic acid, an isostearic acid, a lauric acid, and a caprylic acid.

The content of the nonionic surfactant in the nucleic acid extraction liquid is preferably 0.001 vol % or more, more preferably 0.01 vol % or more, and preferably 1 vol % or less, more preferably 0.1 vol % or less. When the content of the nonionic surfactant is within the above range, the generation of bubbles can be more reliably suppressed, and the efficiency of nucleic acid recovery can be further improved.

The silicone antifoaming agent is preferably an antifoaming agent including a silicone oil and an emulsifier. Alternatively, the silicone antifoaming agent is preferably one obtained by emulsifying the silicone oil with a nonionic surfactant. Examples of the silicone antifoaming agent include Bisfoam GC-302 and Bisfoam ED-10 (manufactured by NISSIN KAGAKU KENKYUSHO CO., LTD.); and Shin-Etsu Silicones (registered trademark) KM-70, KM-71, KM-72, KM-72F, KM-72FS, KM-72S, KM-73, KM-73A, KM-73E, KM-75, KM-7750D, KM-7752, KM-85, KM-89, KM-90, and KM-98 (manufactured by Shin-Etsu Chemical Co., Ltd.).

Examples of the emulsifier include the nonionic surfactant described above and the like.

The content of the silicone antifoaming agent in the nucleic acid extraction liquid is preferably 0.001 vol % or more, more preferably 0.01 vol % or more, and preferably 10 vol % or less, more preferably 0.1 vol % or less. When the content of the silicone antifoaming agent is within the above range, the generation of bubbles can be more reliably suppressed, and the efficiency of nucleic acid recovery can be further improved.

The coprecipitation agent is not particularly limited, and examples thereof include a tRNA, a polyadenine, an acrylamide polymer, a glycogen, a dextran, a polyethylene glycol, a sodium chloride, a lithium chloride, a sodium acetate, and an ammonium acetate. Among them, the coprecipitation agent is preferably a polyadenine. In this case, the efficiency of nucleic acid recovery can be further improved. The number of bases of polyadenine can be, for example, 300 or more and 3,500 or less.

The content of the coprecipitation agent in the nucleic acid extraction liquid is preferably 10 ng/μL or more, more preferably 20 ng/μL or more, and preferably 40 ng/μL or less, more preferably 30 ng/μL or less. When the content of the coprecipitation agent is within the above range, the generation of bubbles can be more reliably suppressed, and the efficiency of nucleic acid recovery can be further improved.

As the nucleic acid extraction liquid, for example, a solution containing a protein denaturant, metal cations, and a polar solvent can be used in addition to the antifoaming agent and the coprecipitation agent. The content of the polar solvent in the nucleic acid extraction liquid is preferably 50% or more.

The protein denaturant has a role of breaking down a higher order structure of a protein by interacting with the protein. As the protein denaturant, for example, a surfactant, a reducing agent, a guanidine derivative, thiourea, urea, a salt thereof, or the like can be used. As the surfactant, for example, a sodium dodecyl sulfate (SDS), a polyoxyethylene sorbitan monolaurate (Tween20), or the like can be used. As the reducing agent, for example, a 2-mercaptoethanol, a dithiothreitol (DTT), or the like can be used. Furthermore, as the salt, for example, a salt such as a guanidine hydrochloride can be used. These protein denaturants may be used singly or in combination of two or more kinds thereof.

The concentration of the protein denaturant in the nucleic acid extraction liquid is not particularly limited, but is preferably 2 mol/L or more, more preferably 4 mol/L or more, still more preferably 8 mol/L or more, and preferably 10 mol/L or less. By setting the concentration of the protein denaturant within the above range, the nucleic acid can be more reliably extracted. Furthermore, when two or more protein denaturants are contained, a total concentration is preferably within the above range.

The metal cations are not particularly limited, and for example, an alkali metal ion, an alkaline earth metal ion, a transition metal ion, or a group 12 metal ion can be used.

Examples of the alkali metal ion include a potassium ion, a sodium ion, a lithium ion, a rubidium ion, a cesium ion, and a francium ion.

Examples of the alkaline earth metal ion include a calcium ion, a magnesium ion, a beryllium ion, a strontium ion, a barium ion, and a radium ion.

Examples of the transition metal ion include a manganese ion, an iron ion, a cobalt ion, a nickel ion, and a copper ion.

Examples of the group 12 metal ion include a zinc ion, a cadmium ion, and a mercury ion.

These metal cations may be used singly or in combination of two or more kinds thereof.

Valence of the metal cations is preferably divalent or more. Examples of the divalent or higher metal cations include the calcium ions and the magnesium ions. When the divalent or higher metal cations are used, the nucleic acid can be recovered more efficiently.

The concentration of the metal cations in the nucleic acid extraction liquid is preferably 0.5 mol/L or more, more preferably 1 mol/L or more, and still more preferably 2 mol/L or more. When the concentration of the metal cations is a lower limit value or more, the nucleic acid can be more efficiently recovered. An upper limit value of the concentration of the metal cations is not particularly limited, but can be, for example, 6 mol/L.

The polar solvent is not particularly limited, and examples thereof include water, a dimethyl sulfoxide (DMSO), an N,N-dimethylformamide (DMF), a dimethylacetamide (DMA), a methoxypropanol, a polyethylene glycol, a pentanediol, a propanediol, an aminoethanol, and a diethanolamine. These polar solvents may be used singly or in combination of two or more kinds thereof. Incidentally, the polar solvent may not be contained in the nucleic acid extraction liquid. Furthermore, the nucleic acid extraction liquid may contain a solvent other than the polar solvent. However, from a viewpoint of more reliably extracting the nucleic acid, it is preferable that a polar solvent such as water is contained in the nucleic acid extraction liquid.

(Nucleic Acid Purification Method)
Microchip;

In the nucleic acid purification method of the present invention, the nucleic acid may be purified using a microchip. An example of the microchip will be described below with reference to the drawings.

FIG. 1 is a schematic plan view showing a microchip used in a nucleic acid purification method according to one embodiment of the present invention. Furthermore, FIG. 2 is a schematic cross-sectional view of a portion taken along the line A-A in FIG. 1.

As illustrated in FIGS. 1 and 2, a microchip 1 has a flow path 2 through which a fluid is delivered. A recovery unit 3 is provided in the middle of the flow path 2. Therefore, the flow path 2 includes an upstream side flow path 2a provided upstream of the recovery unit 3 and a downstream side flow path 2b provided downstream of the recovery unit 3. In addition, a solid phase carrier 4 for adsorbing and purifying a nucleic acid is disposed in the recovery unit 3.

The microchip 1 is a chip used for examination and analysis. The microchip 1 is not particularly limited, but in the present embodiment, as illustrated in FIG. 2, includes a plate-like substrate 5 and a cover member 6. The substrate has a main surface 5a. A recess portion 5b is provided on the main surface 5a side of the substrate 5. The recess portion 5b is provided so as to open toward the main surface side of the substrate 5.

The material constituting the substrate 5 is not particularly limited, and for example, a synthetic resin, a rubber, a metal, or the like can be used. The synthetic resin is not particularly limited, but is preferably a thermoplastic resin. As the thermoplastic resin, for example, a cycloolefin polymer, a cycloolefin copolymer, a polycarbonate, a polymethyl methacrylate, a polypropylene, or the like can be used. These may be used singly or in combination of two or more kinds thereof.

The substrate 5 is preferably formed of a molded body of the thermoplastic resin. A molding method is not particularly limited, and a known molding method can be used. Examples of the molding method include an injection molding, an injection compression molding, a gas assist method injection molding, an extrusion molding, a multilayer extrusion molding, a rotation molding, a hot press molding, a blow molding, and a foam molding. Among them, the injection molding is preferable.

The substrate 5 may be formed by laminating a plurality of synthetic resin sheets. The substrate 5 may include a base sheet and a substrate main body having a through hole provided on the base sheet.

The cover member 6 is provided on the main surface 5a of the substrate 5. The cover member 6 is provided so as to close the recess portion 5b of the substrate 5. The cover member 6 closes the recess portion 5b of the substrate 5 to form the recovery unit 3. Furthermore, in the present embodiment, the upstream side flow path 2a and the downstream side flow path 2b are similarly configured by the cover member 6 closing the recess portion 5b of the substrate 5.

The cover member 6 can be made of, for example, a flexible material such as a resin film. As the resin film, for example, thermoplastic resins such as a cycloolefin polymer, a cycloolefin copolymer, a polycarbonate, a polymethyl methacrylate, or a polypropylene can be used.

Furthermore, the cover member 6 may be made of an elastic member. The elastic member is not particularly limited, but is preferably an elastomer. In addition, in the present invention, the substrate 5 and the cover member 6 may be integrally formed.

In the substrate 5, the flow path 2 described above through which the fluid is delivered is provided. Here, the flow path 2 is a micro flow path. The flow path 2 does not necessarily be the micro flow path, and may have a cross-sectional area larger than that of the micro flow path. However, the flow path 2 being the micro flow path is preferable. Thereby, various analyses can be performed with a trace amount of sample.

The micro flow path refers to a fine flow path in which a micro effect is generated when a fluid is conveyed. In such a micro flow path, the liquid is strongly affected by a surface tension, and exhibits behavior different from that of the liquid flowing through a channel having a normal large size.

Cross-sectional shape and size of the micro flow path are not particularly limited as long as the micro flow path is a flow path in which the micro effect described above occurs. For example, in a case where a pump or gravity is used to cause the fluid to flow in the micro flow path, from the viewpoint of reducing flow path resistance, when the cross-sectional shape of the micro flow path is generally rectangular (including square shape), a length of the short side is preferably 20 μm or more, more preferably 50 μm or more, still more preferably 100 μm or more. From the viewpoint of further downsizing a microfluidic device using the microchip 1, the length of the short side is preferably 5 mm or less, more preferably 1 mm or less, and still more preferably 500 μm or less.

Furthermore, when the cross-sectional shape of the micro flow path is generally circular, a diameter (a minor axis in a case of ellipse) is preferably 20 μm or more, more preferably 50 μm or more, and still more preferably 100 μm or more. From the viewpoint of further downsizing the microfluidic device, the diameter (the minor axis in the case of ellipse) is preferably 5 mm or less, more preferably 1 mm or less, and still more preferably 500 μm or less.

Each step of the nucleic acid purification method of the present invention will be described below.

Extraction Step;

In the extraction step, a sample containing the nucleic acid is brought into contact with a nucleic acid extraction liquid.

In this way, the nucleic acid in the sample is extracted, and a nucleic acid extraction liquid containing the nucleic acid is obtained.

It is preferable that the antifoaming agent and the coprecipitation agent described above are contained in the nucleic acid extraction liquid in advance. In other words, it is preferable that the antifoaming agent and the coprecipitation agent are added to the nucleic acid extraction liquid before the nucleic acid extraction liquid is brought into contact with the sample containing the nucleic acid. In this case, the efficiency of nucleic acid recovery can be further improved. However, the antifoaming agent and the coprecipitation agent may be added to the nucleic acid extraction liquid after the nucleic acid extraction liquid is brought into contact with the sample containing the nucleic acid. In any case, the nucleic acid, the antifoaming agent, and the coprecipitation agent can be mixed.

Examples of the sample containing the nucleic acid include a biological sample containing the nucleic acid such as DNA or RNA. Examples of the biological sample include cells, blood, tissue fluid, urine, feces, and the like. In addition, the sample containing the nucleic acid may be, for example, a sample containing the nucleic acid in an environment such as soil, sea water, or river water, and is not particularly limited.

Nucleic Acid Adsorption Step;

In the nucleic acid adsorption step, the nucleic acid is adsorbed to the solid phase carrier by bringing the nucleic acid extraction liquid containing the nucleic acid into contact with the solid phase carrier.

In the nucleic acid purification method using the microchip 1 illustrated in FIGS. 1 and 2, the nucleic acid extraction liquid after the nucleic acid extraction in the nucleic acid extraction step is injected into the upstream side flow path 2a from an injection port 7a and is delivered to the recovery unit 3. Thereby, the nucleic acid is adsorbed to the solid phase carrier 4 in the recovery unit 3.

The solid phase carrier 4 is a carrier for carrying the nucleic acid. In the present embodiment, the solid phase carrier 4 is an anionic adsorbent. Furthermore, the nucleic acid extraction liquid used in the extraction step contains metal cations.

Therefore, when the sample containing the nucleic acid comes into contact with the nucleic acid extraction liquid, the metal cations are ionically bound to the nucleic acid that is negatively charged. When such an extraction solution after nucleic acid extraction is brought into contact with the anionic adsorbent, the metal cations are ionically bound to the anionic adsorbent as shown in FIG. 3. Thereby, the nucleic acid can be adsorbed to the anionic adsorbent via the metal cations.

Accordingly, in this case, the nucleic acid can be easily adsorbed to the anionic adsorbent via the metal cations. Since the metal cations do not inhibit the extraction of the nucleic acid even when added to the nucleic acid extraction liquid, a step of further adding the solution after the nucleic acid extraction may not be provided as in the conventional method using an alcohol. Therefore, a complicated process is not required.

However, the solid phase carrier 4 may not be an anionic adsorbent, and the nucleic acid extraction liquid used in the extraction step may not contain the metal cations. In other words, the nucleic acid may be adsorbed to the solid phase carrier 4 by another method.

The form of the anionic adsorbent is not particularly limited, and for example, the anionic adsorbent can be used in a form of a film, a filter, a plate, a tube, a fibrous form, or the like. The shape of the anionic adsorbent is preferably a fiber, a particle, or a porous one.

The anionic adsorbent is not particularly limited, and can be composed of, for example, silicon compounds, phosphate minerals, silicate minerals, or aluminosilicate minerals. Examples of the silicon compounds include silica and glass. Examples of the phosphate minerals include a hydroxyapatite. Examples of the silicate minerals include a talc and a montmorillonite. Examples of the aluminosilicate minerals include a zeolite. These may be used singly or in combination of two or more kinds thereof.

The anionic adsorbent is preferably silica fibers or glass fibers, and more preferably the silica fibers. In the present embodiment, the silica fibers are used as the anionic adsorbent. However, the anionic adsorbent may be silica particles or a porous body of silica.

Washing Step;

In the washing step, the solid phase carrier to which the nucleic acid is adsorbed is washed by bringing the washing liquid into contact with the solid phase carrier to which the nucleic acid is adsorbed in the nucleic acid adsorption step.

In the nucleic acid purification method using the microchip 1, the washing liquid is delivered to the recovery unit 3. Thereby, the solid phase carrier 4 on which the nucleic acid is adsorbed is washed.

The washing liquid is not particularly limited, and examples thereof include water, a hydrochloric acid-potassium chloride buffer, a glycine-hydrochloric acid buffer, a citric acid-sodium citrate buffer, and a citric acid-phosphate buffer. These may be used alone or in combination of two or more.

The pH of the washing liquid is preferably 5.0 or less, and more preferably 4.0 or less. When the pH of the washing liquid is the above upper limit value or less, unnecessary metal ions can be more reliably removed without desorbing the nucleic acid adsorbed to the anionic adsorbent, and the amplification of the nucleic acid in the subsequent step can be even less likely to be inhibited. In addition, in this case, since alcohol that inhibits a nucleic acid amplification reaction is not used in the washing liquid, an operation of removing the alcohol before the nucleic acid amplification reaction is unnecessary, and the nucleic acid can be purified more easily.

Moreover, the lower limit value of the pH of the washing liquid can be, for example, 2.0.

Nucleic Acid Recovery Step;

Next, the recovery liquid is brought into contact with the solid phase carrier washed in the washing step to isolate the nucleic acid from the anionic adsorbent and recover the nucleic acid.

Specifically, in the nucleic acid purification method using the microchip 1, the recovery liquid is delivered to the recovery unit 3, the nucleic acid is delivered to the downstream side flow path 2b side while being isolated from the solid phase carrier 4, and the nucleic acid is recovered from a recovery port 7b.

The recovery liquid is preferably a solution that does not inhibit the nucleic acid amplification reaction. In this case, the accuracy of analysis and examination in the subsequent process can be further enhanced.

As the recovery liquid, a buffer, a reagent for nucleic acid amplification, or the like can be used.

As the buffer, trishydroxymethylaminomethane (Tris), N-tris(hydroxymethyl)methyl-2-aminoethanesulfonic acid (TES), tricine, PIPES, ACES, MOPSO, BES, MOPS, HEPES, TAPSO, POPSO, HEPSO, EPPS, Bicine, TAPS, a phosphate buffer, or the like can be used.

As the reagent for nucleic acid amplification, TaqPath 1-Step Multiplex Master Mix, TaqMan Gene Expression Master Mix, TaqMan Fast Advanced Master Mix Mix, TaqPath qPCR Master Mix, CG, TaqMan Fast Virus 1-Step Master Mix (manufactured by Thermo Fisher), or the like can be used.

These may be used singly or in combination of two or more kinds thereof.

The pH of the buffer is preferably 6.0 or more, more preferably 7.0 or more, and still more preferably 8.0 or more. In this case, the nucleic acid can be recovered more efficiently. The upper limit value of the pH of the buffer is not particularly limited, but can be, for example, 9.0.

The concentration of the buffer is preferably 5 mmol/L or more, more preferably 10 mmol/L or more, and preferably 50 mmol/L or less, more preferably 30 mmol/L or less. When the concentration of the buffer is within the above range, the nucleic acid can be recovered more efficiently.

Furthermore, in the nucleic acid adsorption step, the washing step, and the nucleic acid recovery step, the liquid can be delivered using, for example, a micropump. The micropump is not particularly limited, and examples thereof include an optical gas generation tape. The optical gas generation tape is a tape capable of generating gas by light irradiation.

Note that, in the present embodiment, the example of using the microchip 1 illustrated in FIGS. 1 and 2 has been described, but a structure is not particularly limited as long as it is a microchip having the micro flow path described above.

Furthermore, in the nucleic acid purification method of the present invention, the nucleic acid may be purified using a spin column or magnetic beads. Also in this case, due to an effect of the antifoaming agent, wettability is improved and foaming can be suppressed, so that filter filtration time can be further shortened. In addition, by mixing the nucleic acid and the coprecipitation agent, the efficiency of nucleic acid recovery can be further enhanced. Therefore, also in this case, the nucleic acid can be efficiently purified.

[Nucleic Acid Purification Kit]

The nucleic acid purification kit of the present invention includes the nucleic acid extraction liquid of the present invention described above. The nucleic acid purification kit of the present invention may further include a washing liquid, a recovery liquid, an anionic adsorbent, and the like. According to the nucleic acid purification kit of the present invention, a nucleic acid can be efficiently purified by using the nucleic acid purification method described above. As the washing liquid, the recovery liquid, and the anionic adsorbent, the same ones as those described above in the nucleic acid purification method can be used.

The following will clarify the present invention by giving specific examples and comparative examples of the present invention. Note that the present invention is not limited to the following examples.

Example 1

In Example 1, the microchip 1 illustrated in FIGS. 1 and 2 was produced as follows.

The cycloolefin polymer was used as a material constituting the substrate 5, and the cycloolefin polymer was injection-molded to produce the substrate 5 having the recess portion 5*b*. In addition, a sealing tape was used for the cover member 6, and the recess portion 5*b* of the substrate 5 was closed with the sealing tape to produce the microchip 1. Furthermore, in the recovery unit 3, the silica fibers as the anionic adsorbent were disposed as the solid phase carrier 4 (2 mmφ, thickness 0.8 mm). In addition, a width of the flow path 2 was 0.8 mm, and a depth was 0.8 mm.

Using such microchip 1, a nucleic acid (RNA) was recovered as follows. Furthermore, the liquid delivery was performed using an optical gas generation tape.

First, a nucleic acid extraction liquid in which nasal mucus was suspended in an aqueous solution containing the nonionic surfactant (Bisfoam ASV manufactured by NISSIN KAGAKU KENKYUSHO CO., LTD.) as the antifoaming agent, polyadenine (Carrier RNA manufactured by QIAGEN, product number "1017647", hereinafter referred to as cRNA) as the coprecipitation agent, 4 mol/L of urea, 4 mol/L of guanidine hydrochloride, 2 mol/L of calcium chloride, and Tris-HCl Buffer (pH 7.0) was prepared. The concentration of the nonionic surfactant in the nucleic acid extraction liquid was 0.1 vol %. The concentration of polyadenine (cRNA) in the nucleic acid extraction liquid was 20 ng/μL.

Next, a sample containing 1 μL of the nucleic acid (RNA) (virus; 60,000 copies) was added to 150 μL of the nucleic acid extraction liquid to extract the nucleic acid.

Then, the nucleic acid extraction liquid after the nucleic acid extraction was delivered from the upstream side flow path 2*a* to the recovery unit 3 to adsorb the nucleic acid to the silica fibers of the recovery unit 3.

Next, 400 μL of the washing liquid (10 mmol/L, KCl—HCl Buffer (pH 2.0)) was delivered to the recovery unit 3 to wash the silica fibers carrying the nucleic acid, and the washing liquid after delivery was recovered. The recovery liquid (21 μL) (10 mmol/L, Tris-HCl Buffer (pH 8.0)) was delivered to the recovery unit 3, and the nucleic acid (RNA) carried in the recovery unit 3 was isolated and recovered.

Example 2

The nucleic acid (RNA) was isolated and recovered in the same manner as in Example 1 except that the silicone antifoaming agent (Bisfoam GC-302 manufactured by NISSIN KAGAKU KENKYUSHO CO., LTD.) was used as the antifoaming agent.

Examples 3 to 5

The nucleic acid (RNA) was isolated and recovered in the same manner as in Example 1 except that the concentration of the nonionic surfactant as the antifoaming agent was changed as shown in Table 2 below.

Examples 6 to 9

The nucleic acid (RNA) was isolated and recovered in the same manner as in Example 2 except that the concentration of the silicone antifoaming agent as the antifoaming agent was changed as shown in Table 2 below.

Example 10

A sample containing 1 μL of the nucleic acid (RNA) (virus; 100,000 copies) was added to 150 μL of a nucleic acid extraction liquid (aqueous solution containing 4 mol/L of urea, 4 mol/L of guanidine hydrochloride, 2 mol/L of calcium chloride, and Tris-HCl Buffer (pH 7.0)) to extract the nucleic acid. After the nucleic acid was extracted, the nonionic surfactant (Bisfoam ASV manufactured by NISSIN KAGAKU KENKYUSHO CO., LTD.) as the antifoaming agent and the polyadenine (cRNA manufactured by QIAGEN, product number "1017647") as the coprecipitation agent were added. The concentration of the nonionic surfactant in the nucleic acid extraction liquid was 0.1 vol %. The concentration of polyadenine (cRNA) in the nucleic acid extraction liquid was 20 ng/μL. Except for the above, the nucleic acid (RNA) was isolated and recovered in the same manner as in Example 1.

Example 11

The nucleic acid (RNA) was isolated and recovered in the same manner as in Example 10 except that the silicone antifoaming agent (Bisfoam GC-302 manufactured by NISSIN KAGAKU KENKYUSHO CO., LTD.) was used as the antifoaming agent.

Comparative Example 1

The nucleic acid (RNA) was isolated and recovered in the same manner as in Example 1 except that the antifoaming agent and the coprecipitation agent were not used.

Comparative Example 2

The nucleic acid (RNA) was isolated and recovered in the same manner as in Example 1 except that no coprecipitation agent was used.

Comparative Example 3

The nucleic acid (RNA) was isolated and recovered in the same manner as in Example 2 except that no coprecipitation agent was used.

Comparative Example 4

The nucleic acid (RNA) was isolated and recovered in the same manner as in Example 1 except that no antifoaming agent was used.

Comparative Example 5

The nucleic acid (RNA) was isolated and recovered in the same manner as in Example 1 except that a cationic surfactant (QUARTAMIN 24P manufactured by Kao Corporation) was used instead of the antifoaming agent in Example 1.

Comparative Example 6

The nucleic acid (RNA) was isolated and recovered in the same manner as in Example 1 except that the anionic surfactant (DEMOL NL manufactured by Kao Corporation) was used instead of the antifoaming agent in Example 1.

[Evaluation]

(Evaluation of Antifoaming Effect)

FIGS. 4 to 5 are photographs for confirming the number of bubbles generated during the liquid delivery in Examples 1 to 2. FIG. 6 is a photograph for confirming the number of bubbles generated during the liquid delivery in Comparative Example 1.

As shown in FIGS. 4 to 6, it can be seen that the generation of bubbles is suppressed in Examples 1 to 2 as compared with Comparative Example 1.

Furthermore, in Example 3 to 9 and Comparative Examples 2 to 6, the same observation was performed, and the antifoaming effect was determined according to the following evaluation criteria based on the number of bubbles generated during the liquid delivery.

<Evaluation Criteria>

○: 5 or less x: 6 or more and 10 or less xx: 11 or more (Recovery Rate)

In Examples 1 to 11 and Comparative Examples 1 to 6, a ratio of RNA in the recovery liquid was evaluated. Specifically, an RT-PCR reaction solution was prepared using 2 μL of the recovery liquid, the primer, and TaqPath 1-Step Multiplex Master Mix (manufactured by Thermo Fisher). Furthermore, as a standard, the RT-PCR reaction solution (3 levels of nucleic acid concentration: 50,000 copies/μL, copies/μL, and 500 copies/μL) containing 2 μL of a solution obtained by extracting and purifying the same virus using QIAamp Viral RNA Mini Kit manufactured by QIAGEN was also prepared. Next, the RT-PCR reaction solution and the standard RT-PCR reaction solution prepared from the recovery liquid were amplified using a thermal cycler "CFX96 (Bio-Rad)". For amplification, a reverse transcription reaction was performed at 50° C. for 30 seconds, then an initial denaturation was performed at 95° C. for 20 seconds, and a PCR cycle was performed 45 times at 95° C. for 3 seconds and 60° C. for 5 seconds. After amplification, an RNA recovery rate (a recovery rate) was calculated according to the following calculation formula, based on the amount of nucleic acid automatically calculated by CFX96 from a standard.

Recovery rate (%)={(Amount of nucleic acid calculated by CFX96×Amount of recovery liquid/2)×100}/3,0000

Furthermore, in Examples 1 to 9 and Comparative Examples 1 to 6, an overall evaluation of the antifoaming effect and the recovery rate was determined according to the following evaluation criteria.

<Evaluation Criteria>

○: The recovery rate was κ% or more, and the above-mentioned evaluation for the antifoaming effect was ○.

x: The recovery rate was 1% or more and less than 5% regardless of the antifoaming effect, or the above-mentioned evaluation for the antifoaming effect was x regardless of the recovery rate.

xx: The recovery rate was less than 1% regardless of the antifoaming effect, or the above-mentioned evaluation for the antifoaming effect was xx regardless of the recovery rate.

The results are shown in Tables 1 to 3 below.

TABLE 1

| | Example 1 | Example 2 | Comparative Example 1 | Comparative Example 2 | Comparative Example 3 | Comparative Example 4 | Comparative Example 5 | Comparative Example 6 |
|---|---|---|---|---|---|---|---|---|
| Antifoaming agent | Nonionic surfactant | Silicone antifoaming agent | — | Nonionic surfactant | Silicone antifoaming agent | — | Cationic surfactant | Anionic surfactant |
| Coprecipitation agent | cRNA | cRNA | — | — | — | cRNA | cRNA | cRNA |

TABLE 1-continued

|  | Example 1 | Example 2 | Comparative Example 1 | Comparative Example 2 | Comparative Example 3 | Comparative Example 4 | Comparative Example 5 | Comparative Example 6 |
|---|---|---|---|---|---|---|---|---|
| Antifoaming effect | ○ | ○ | xx | ○ | ○ | xx | xx | x |
| Recovery rate | 51.5% | 42.5% | 0.29% | 0.24% | 0.57% | — | — | — |
| Overall evaluation | ○ | ○ | xx | xx | xx | xx | xx | x |

TABLE 2

|  | Example 3 | Example 4 | Example 1 | Example 5 | Example 6 | Example 7 | Example 2 | Example 8 | Example 9 | Comparative Example 1 |
|---|---|---|---|---|---|---|---|---|---|---|
| Antifoaming agent | Nonionic surfactant | Nonionic surfactant | Nonionic surfactant | Nonionic surfactant | Silicone antifoaming agent | Silicone antifoaming agent | Silicone antifoaming agent | Silicone antifoaming agent | Silicone antifoaming agent | — |
| Coprecipitation agent | cRNA | cRNA | cRNA | cRNA | cRNA | cRNA | cRNA | cRNA | cRNA | — |
| Concentration of antifoaming agent | 0.001 vol % | 0.01 vol % | 0.10 vol % | 1 vol % | 0.001 vol % | 0.01 vol % | 0.10 vol % | 1 vol % | 10 vol % | — |
| Antifoaming effect | ○ | ○ | ○ | ○ | ○ | ○ | ○ | ○ | ○ | xx |
| Recovery rate | 42.7% | 44.9% | 51.5% | 69.8% | 28.4% | 43.4% | 42.5% | 32.3% | 9.8% | 0.29% |
| Overall evaluation | ○ | ○ | ○ | ○ | ○ | ○ | ○ | ○ | ○ | xx |

TABLE 3

|  | Example 1 | Example 10 | Example 2 | Example 11 | Comparative Example 1 |
|---|---|---|---|---|---|
| Antifoaming agent | Nonionic surfactant | Nonionic surfactant | Silicone antifoaming agent | Silicone antifoaming agent | — |
| Coprecipitation agent | cRNA | cRNA | cRNA | cRNA | — |
| Addition timing of coprecipitation agent/antifoaming agent | Pre-add to nucleic acid extraction liquid | Add to nucleic acid extraction liquid after extraction | Pre-add to nucleic acid extraction liquid | Add to nucleic acid extraction liquid after extraction | — |
| Recovery rate | 51.5% | 46.7% | 42.5% | 52.4% | 0.29% |

DESCRIPTION OF REFERENCE SYMBOLS

1 Microchip
2 Flow path
2a Upstream side flow path
2b Downstream side flow path
3 Recovery unit
4 Solid phase carrier
5 Substrate
5a Main surface
5b Recess portion
6 Cover member
7a Injection port
7b Recovery port

The invention claimed is:

1. A nucleic acid purification method, comprising:
a step of mixing a sample containing a nucleic acid with an antifoaming agent and a coprecipitation agent, thus obtaining a nucleic acid extraction liquid containing the nucleic acid; and
a step of purifying the nucleic acid,
wherein
the antifoaming agent is at least one of a nonionic surfactant and a silicone antifoaming agent,
a content of the antifoaming agent in the nucleic acid extraction liquid containing the nucleic acid is 0.001 vol % or more and 1 vol % or less, and
the coprecipitation agent is a polyadenine.

2. The nucleic acid purification method according to claim 1, wherein the nucleic acid is mixed with the antifoaming agent and the coprecipitation agent, and then the nucleic acid is adsorbed on a solid phase carrier and purified.

3. The nucleic acid purification method according to claim 1, further comprising:
a step of preparing a nucleic acid extraction liquid containing the antifoaming agent and the coprecipitation agent in advance, wherein
the nucleic acid is mixed with the antifoaming agent and the coprecipitation agent by bringing a sample containing the nucleic acid into contact with the nucleic acid extraction liquid.

4. The nucleic acid purification method according to claim 1, wherein the antifoaming agent is the nonionic surfactant.

5. The nucleic acid purification method according to claim 4, wherein the nonionic surfactant is at least one selected from a group consisting of a polyoxyalkylene alkyl ether, a polyoxyethylene branched alkyl ether, a polyoxyethylene octylphenyl ether, a polyoxyethylene distyrenated phenyl ether, a polyoxyethylene phytosteryl ether, a polyoxyalkylene fatty acid ester, a polyoxyalkylene glyceryl ether, a sorbitan fatty acid ester, a lauryl-β-D-maltoside, a polyoxyethylene alkylamine, a palm kernel oil fatty acid diethanolamide, and a digitonin.

6. The nucleic acid purification method according to claim 4, wherein the nonionic surfactant is a mixture of a polyoxyalkylene alkyl ether and a polyoxyalkylene fatty acid ester.

7. The nucleic acid purification method according to claim 1, wherein the antifoaming agent is the silicone antifoaming agent.

8. The nucleic acid purification method according to claim 7, wherein the silicone antifoaming agent includes a silicone oil and an emulsifier.

9. The nucleic acid purification method according to claim 7, wherein the silicone antifoaming agent is obtained by emulsifying the silicone oil with the nonionic surfactant.

* * * * *